(12) United States Patent
Benz et al.

(10) Patent No.: US 9,301,818 B2
(45) Date of Patent: Apr. 5, 2016

(54) ABUTMENT AND DENTAL-PROSTHETIC ARRANGEMENT HAVING SUCH AN ABUTMENT

(75) Inventors: Roland Benz, Ulm (DE); Wilfried Boehm, Senden (DE)

(73) Assignee: Bredent GmbH & Co. KG, Senden (DE)

( * ) Notice: Subject to any disclaimer, the term of this patent is extended or adjusted under 35 U.S.C. 154(b) by 0 days.

(21) Appl. No.: 13/877,981

(22) PCT Filed: Oct. 7, 2010

(86) PCT No.: PCT/EP2010/064998
§ 371 (c)(1),
(2), (4) Date: Apr. 17, 2013

(87) PCT Pub. No.: WO2012/045356
PCT Pub. Date: Apr. 12, 2012

(65) Prior Publication Data
US 2013/0209958 A1     Aug. 15, 2013

(51) Int. Cl.
A61C 8/00         (2006.01)

(52) U.S. Cl.
CPC .............. *A61C 8/0068* (2013.01); *A61C 8/005* (2013.01); *A61C 8/0037* (2013.01); *A61C 8/0048* (2013.01); *A61C 8/0056* (2013.01); *A61C 8/0075* (2013.01); *A61C 8/0089* (2013.01)

(58) Field of Classification Search
CPC ...... A61C 8/001; A61C 8/005; A61C 8/0053; A61C 8/0056; A61C 8/0074
USPC .................................. 433/172–195
See application file for complete search history.

(56) References Cited

U.S. PATENT DOCUMENTS

| | | | | |
|---|---|---|---|---|
| 5,116,225 A | * | 5/1992 | Riera | 433/173 |
| 5,195,891 A | * | 3/1993 | Sulc | 433/173 |
| 5,362,235 A | * | 11/1994 | Daftary | 433/172 |
| 5,571,015 A | | 11/1996 | Siegmund | |

(Continued)

FOREIGN PATENT DOCUMENTS

| EP | 2127612 A1 * 12/2009 | ............... A61C 8/00 |
|---|---|---|
| EP | 2 127 612       3/2010 | |

(Continued)

OTHER PUBLICATIONS

International Search Report of PCT/EP2010/064998, date of mailing Aug. 17, 2011.

*Primary Examiner* — Cris L Rodriguez
*Assistant Examiner* — Matthew Saunders
(74) *Attorney, Agent, or Firm* — Collard & Roe, P.C.

(57) ABSTRACT

The invention relates to an angled abutment for a dental-prosthetic arrangement, in which the abutment is divided into a first sub-component and a second sub-component, wherein the first sub-component can be fixed by means of a fixing screw to an implant and has a tool opening through which a tool is able to engage to reach the screw head of the fixing screw. After the first sub-component has been fixed to an implant, the second sub-component can be connected to the first sub-component, preferably via a screwed connection, and at the same time completely covers the tool opening of the first sub-component. A retaining structure facing away from the first sub-component is formed on the second sub-component and interacts with a counter-retaining structure on a prosthesis to provide a releasable connection, which can be produced without tools, between the abutment and the prosthesis.

16 Claims, 4 Drawing Sheets

(56) References Cited

U.S. PATENT DOCUMENTS

Figure 1:
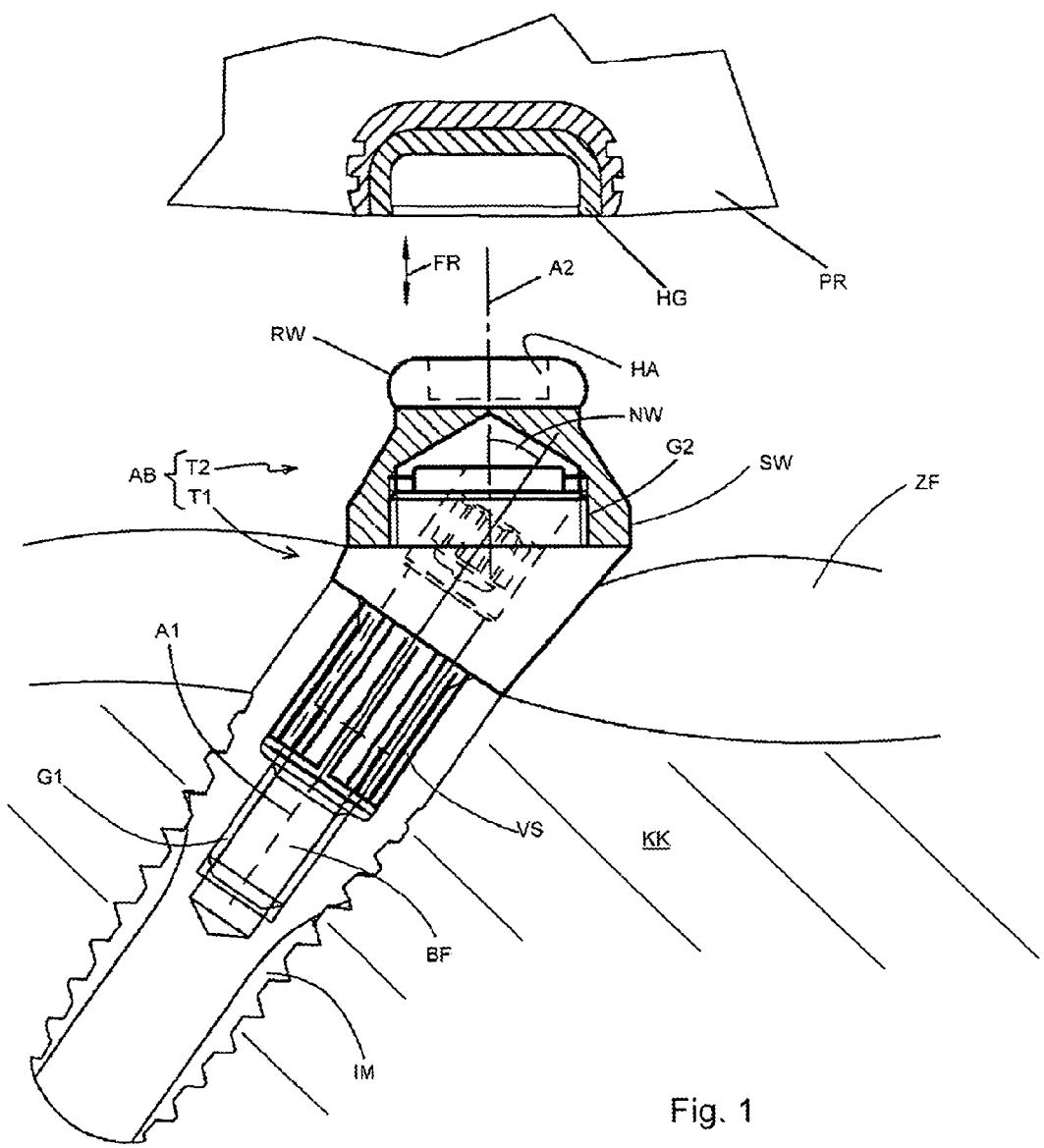

| | | |
|---|---|---|
| 6,663,388 B1 * | 12/2003 | Schar et al. .................. 433/173 |
| 8,142,193 B2 | 3/2012 | Bar Shalom |
| 2008/0153063 A1 | 6/2008 | Mullaly et al. |
| 2008/0227058 A1 | 9/2008 | Karmon |
| 2009/0117520 A1 * | 5/2009 | Kikuchi ........................ 433/174 |
| 2009/0298013 A1 * | 12/2009 | Baruc ........................... 433/174 |
| 2010/0075277 A1 * | 3/2010 | Wils .............................. 433/193 |
| 2010/0129774 A1 | 5/2010 | Martinez et al. |
| 2011/0097687 A1 * | 4/2011 | Engman ........................ 433/174 |

FOREIGN PATENT DOCUMENTS

| | | | |
|---|---|---|---|
| EP | 2 168 531 | 3/2010 | |
| EP | 2 266 498 | 12/2010 | |
| EP | 2266498 A1 * | 12/2010 | ............... A61C 8/00 |
| WO | WO 2007/059595 | 5/2007 | |
| WO | WO 2008/141404 | 11/2008 | |

* cited by examiner

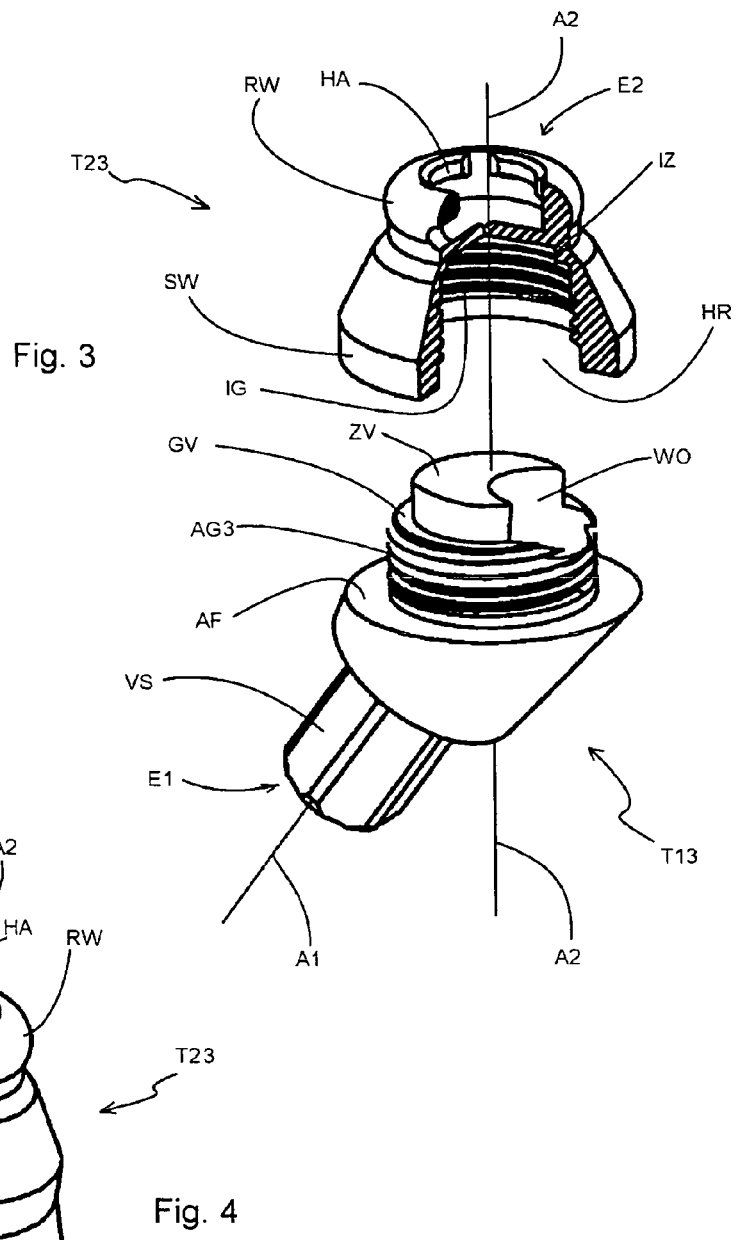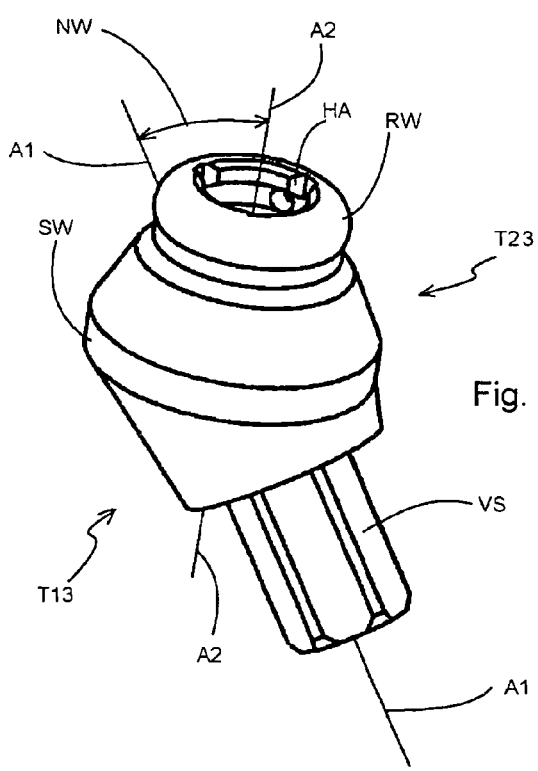

ABUTMENT AND DENTAL-PROSTHETIC ARRANGEMENT HAVING SUCH AN ABUTMENT

CROSS REFERENCE TO RELATED APPLICATIONS

This application is the National Stage of PCT/EP2010/064998 filed on Oct. 7, 2010, the disclosure of which is incorporated by reference. The international application under PCT article 21(2) was not published in English.

The invention relates to an abutment and to a dental-prosthetic arrangement.

Abutments form connection elements between osseointegrated implants and dental prostheses in dental-prosthetic applications. After an implant that has been inserted, typically screwed, into a bore in the jaw bone, has healed in place, which implant is intended to permanently remain in the jaw bone, the abutment is attached to the implant and a dental prosthesis is placed onto the abutment as a further structure. In the case of complete prostheses or in the case of partial prostheses covering a larger jaw section, it is known to assign multiple implants and abutments to a prosthesis. In particular, it is known for complete prostheses to hold the entire prosthesis on four abutments, of which two are disposed offset toward the rear in the direction of the jaw joint. The holding structures of the multiple abutments lie approximately in one plane, and setting the prosthesis onto the holding structures of the abutment takes place essentially perpendicular to this plane.

In particular for the abutments disposed offset in the direction of the jaw joint, there is frequently the problem, for example in older patients and/or if the original teeth have already been missing for a long time, that the jaw has atrophied greatly and insufficient bone substance is available for an implant bore perpendicular to the stated plane.

From EP 2 127 612 A1, it is known, particularly for those cases of little bone substance, to structure the implant bore in the jaw bone at a slant relative to the said plane, and to undertake direction equalization for an angled abutment, in order to align the holding structure, once again, for a set-on direction of the holding structure that runs essentially perpendicular to the plane. The abutments described for this purpose possess a first axis at a first, implant-side end, which is defined by the screw axis of a fastening screw, and a second axis, defined by the holding structure and its joining direction, in which the prosthesis is set onto or removed from the abutment, at the end facing away from the implant. The second axis runs at an incline of at least 10° relative to the first axis. In the direction of the second axis, projections on the abutment in the form of a spherical head or a truncated cone with an inside thread are provided as holding structures. In order to fasten the abutment onto the implant, a tool opening in the abutment is configured between the first and the second end, as an extension of the first axis. The tool opening allows application of a turning tool to the screw head of the fastening screw, in order to screw it into an inside bore of the implant and tighten it at a defined torque. At the first end of the abutment, an anti-turn device, for example in the shape of a hexagon, can be provided, which engages into a corresponding recess in the implant. Also, what are called snap structures, having a ring bead that runs around the second axis, are known as holding structures.

Examples of angled abutments, also referred to as angulated abutments, are also given in WO 2008/141404 A1 or in FIG. 9 of US 2008/0227058 A1. In U.S. Pat. No. 5,571,015 or WO 2007/059595 A2, wedge bodies for direction compensation are described. Furthermore, abutments having internal, clampable ball joints are known. For individual dental prostheses that are firmly bonded or screwed in place, particularly in the case of front teeth, abutments having a slight internal deflection between an implant and an upper section that holds a crown are known.

The present invention is based on the task of indicating an angulated abutment and a dental-prosthetic arrangement having such an abutment, particularly with a removable prosthesis, having advantageous properties in terms of handling and hygiene.

Solutions according to the invention are described in the independent claims. The dependent claims contain advantageous embodiments and further developments of the invention.

The division of the abutment into a first body element that can be fastened to an implant by means of the fastening screw, and a second body element that contains the holding structure for the prosthesis, allows simple and reliable fastening of the abutment onto the implant, in advantageous manner, and at least partial or preferably complete covering of the tool opening formed in the first body element, by means of the second body element, so that the risk of collection of contaminants in depressions inaccessible to the user is reduced or entirely avoided. In this connection, the use of a tool, in usual manner, for fastening the first body element onto the implant, is possible without hindrance. Covering of the tool opening only takes place afterward, by means of connecting the second body element with the first.

Connection of the two body elements can take place by means of bonding, for example, but preferably contains a screw connection having a second thread about the second axis. Connection by way of a screw connection, which preferably contains a fine thread, allows simple and secure connection. At the same time, a screw connection can advantageously be loosened in destruction-free manner, so that in the event of damage to or wear of the holding structure, only the second body element has to be replaced, whereby the first body element remains fastened to the implant, undamaged and without any change in position, and therefore the stress for the wearer of the prosthesis, in this connection, is particularly low. The separate replaceability of the second body element advantageously also allows a simple switch to a different holding system, with different holding structures, on the side of the abutment.

Typically, an implant system contains abutments that are angulated to different degrees, whereby an inclination angle between the first and the second axis typically amounts to at least 10°. For abutments having different such inclination angles, it is advantageous that uniform second body elements can be used.

Figure 2:
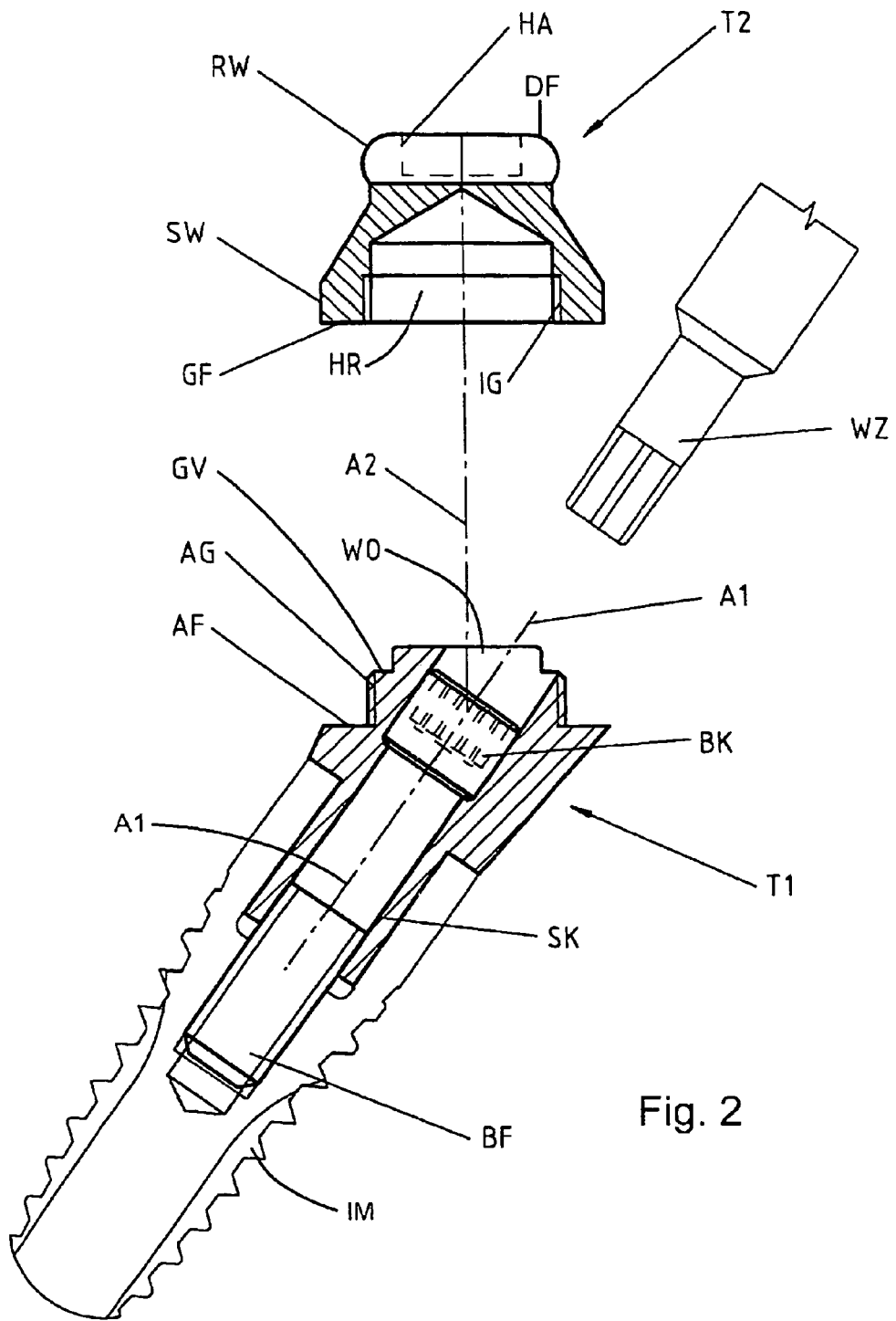
Figure 5:
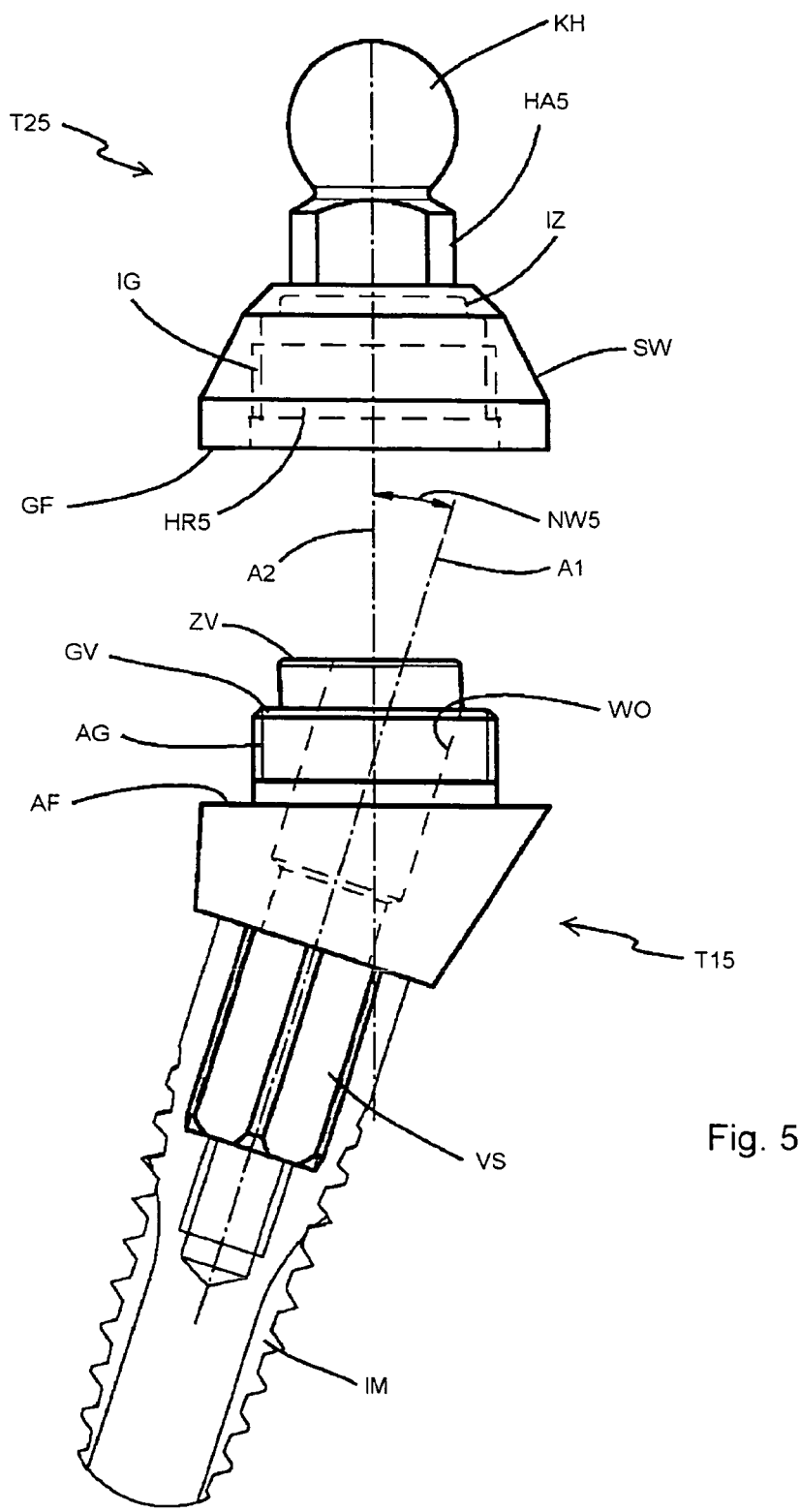

The invention will be illustrated in detail below, using preferred exemplary embodiments and making reference to the figures. These show:

FIG. 1 a first embodiment of an abutment,

FIG. 2 an abutment according to FIG. 1, with separate body elements,

FIG. 3 separate body elements in a slanted view,

FIG. 4 the body elements according to FIG. 3 in the connected state,

FIG. 5 body elements of a second embodiment of an abutment.

FIG. 1 schematically shows a dental-prosthetic arrangement having an implant IM anchored in a jaw bone KK, an abutment AB fastened onto the implant with a first end, having body elements T1 and T2, as well as a prosthesis PR having a counter-holding structure HG to a holding structure RW disposed on the second end of the abutment, on the second body element T2 of the abutment, whereby jaw and prosthesis are shown only in the relevant detail, and the prosthesis is shown in a position raised up from the abutment and the jaw. The implant IM also extends through gums ZF that surround the jaw bone KK.

The implant IM, in usual manner, possesses a first inside thread, into which a fastening screw BF for fastening the abutment AB onto the implant IM is screwed by way of a first threaded connection G1. The screw axis of the fastening screw BF or of the first inside thread G1 forms a first axis A1 of the abutment, which corresponds to the direction of the channel drilled into the jaw to insert the implant. In the implant, a recess can be introduced from its end that faces away from the jaw bone, also in known manner, which recess is not circular in cross-section and engages into an anti-turn structure VS of the abutment, which is also not circular. Cross-sections of the recess and the anti-turn structure VS can be configured in six-fold manner, for example, with rotation symmetry about the first axis A1, so that the implant can be screwed into the drilled channel, to a screw-in depth that is optimal for integration into the bone and projection above the bone, and in this connection, a rotational position about the first axis that is suitable for the desired orientation of the abutment can be achieved with only slight variation of the screw-in depth.

In order to hold a prosthesis PR on the jaw of the patient, a holding structure is configured on the abutment, which structure interacts with a counter-holding structure HG in the prosthesis, and determines a joining direction FR in which the holding structure and the counter-holding structure are joined together to produce a holding connection, or can be separated from one another to release a holding connection. The joining direction runs essentially parallel to a second axis A2 provided by the holding structure on the abutment. Slight angle deviations are permissible in the usual holding connection in the spherical head technique, ring-bead technique, cone technique, or others.

In the example shown, the holding structure RW is formed on the second body element T2 of the abutment and structured as a radially projecting ring bead. The second body element T2 is connected with the first body element by way of a second threaded connection G2. To produce the connection between the two body elements or for releasing the connection, the second body element T2 can be rotated about the second axis A2.

The body elements T1 and T2, separated from one another, are shown in FIG. 2 in a side view corresponding to FIG. 1.

The first body element T1 has a contact surface AF on its end facing away from the abutment and facing the second body element T2, on which surface a counter-surface GF, as an end edge of a side wall SW of the second body element T2, supports itself in the connected state of the two body elements. A threaded extension GV is disposed projecting in the direction of the second axis A2, toward the second body element T2, against this contact surface AF, which threaded extension GV possesses an outside thread AG.

In the installation position shown in FIG. 2, a cavity HR is formed in the second body element T2, facing the first body element T1, which cavity is closed on all sides, with the exception of the opening that faces the first body element T1. As a result, the second body element T2 has approximately the shape of a cap. The side wall SW that radially delimits the cavity HR with regard to the second axis A2 has an inside thread IG on its inner surface, which thread is configured to engage with the outside thread AG of the threaded extension GV on the first body element, to produce the second threaded connection G2.

A screw channel SK is formed in the first body element T1, through which channel the fastening screw BF passes with its shaft. The screw head BK of the fastening screw is supported axially on the upper end of the screw channel, with reference to the first axis A1. In an extension of the first axis, facing away from the first end E1 of the abutment and therefore from the implant, a tool opening WO is provided, by means of which a turning tool WZ can be brought into engagement with a tool engagement location in the screw head BK, in order to screw the fastening screw BF into the first thread G1 of the implant, and thereby to fasten the first body element T1 onto the implant.

When the first body element T1 is fastened onto the implant, the second body element T2 is screwed onto the first body element T1, by way of the second threaded connection G2 with outside thread AG and inside thread IG, and in this connection completely covers the tool opening WO and lies against the contact surface AF of the first body element with the counter-surface GF.

To screw the second body element T2 onto the first body element T1, a further tool engagement location, for example in the form of a depression HA relative to an end surface DF of the second body element T2 on the second end E2 of the abutment can be provided on the second body element T2. A tool engagement location can also be formed by means of a different structure not having rotation symmetry, on the second body element T2. However, the second body element can also be screwed onto or released from the first body element T1 solely by means of friction-fit engagement of a tool.

FIG. 3, in a slanted perspective view, shows two body elements T13 and T23, which correspond to the body elements T1 and T2 according to FIG. 1 and FIG. 2, to a great extent, and differ from these only in details of the second threaded connection and additional centering devices. The same components are provided with the same reference symbols as in FIGS. 1 and 2. In this embodiment, inside thread IG and outside thread AG do not reach all the way to the counter-surface GF or the contact surface AF, respectively. Advantageously, a centering extension ZV in the form of a circular cylinder can project from the threaded extension GV in the direction of the second body element, which threaded extension GV interacts with an inner centering structure IZ in the second body element, in a manner that centers the two body elements, relative to one another, about the second axis A2.

From FIG. 3, it is clearly evident that the tool opening WO partly intersects the outside thread AG3 of the first body element T13. However, the diameter of the outside thread can advantageously be selected to be relatively large, by means of the formation of the first connection structure on the side of the first body element for the connection of the two body elements, as an outside thread on a threaded extension, so that only part of the outside thread is disturbed by the tool opening WO, and despite this disruption, a secure connection exists between the first and the second body element.

By means of the division of the abutment into a first and a second body element, fastening of the first body element by means of the tool WZ can be undertaken in conventional, simple manner, for one thing, and for another, a hygienically particularly advantageous arrangement can be created by means of the second body element, because after the second body element, which is not removed by the user himself/herself, has been set on, penetration of contaminants into the tool opening WO is reliably prevented. At the same time, releasability of the prosthesis from the abutment is maintained without restrictions, and furthermore, the second body element can be removed again, with little effort, in the event of damage to or wear of the ring bead RW that forms the holding structure RW, or in the event of a switch to a different holding system, and replaced with a different second body element.

For a secure connection without additional measures such as bonding, for example, outside thread AG and inside thread IG are advantageously structured as fine threads having a thread pitch of maximally 0.5 mm. The diameter of the second threaded connection G2 is advantageously greater, particularly at least 20% greater than the thread diameter of the first threaded connection G1 between fastening screw and implant. The diameter of the second threaded connection G2 advantageously amounts to at least 2 mm.

The inclination angle indicated with NW in FIG. 1, between the first axis A1 and the second axis A2, advantageously amounts to at least 10° for an abutment angulated in this manner. Advantageously, abutments having different angulations are present within an implant system, whereby if sufficient bone substance is present, preferably non-angled abutments, which are known as such, are used.

FIG. 5, in a side view similar to FIG. 2, shows a different embodiment of a two-part abutment according to the invention, having a first body element T15 and a second body element T25, in an individual representation in which they are separated from one another. In the example shown in FIG. 5, the inclination angle NW5 between the first axis A1 and the second axis A2 amounts to only approximately 17.5°. Because of the smaller angle, the tool opening WO in the second body element passes through the threaded extension GV without intersecting the outside thread AG. The fastening screw is not shown in FIG. 5.

The second body element T25 in FIG. 5 has a spherical head KH as the holding structure, which is known and usual as a holding structure. A tool engagement location HA5 is provided, in this example, in the axial direction between the holding structure HA5 and the side wall SW.

The abutment according to FIG. 5, like the embodiment according to FIG. 3, shows centering devices in the form of a centering extension ZV on the first body element T15 and an inner centering structure IZ in the second body element T25, which enter into reciprocal engagement when the second body element T25 is screwed onto the first body element T15, and in this connection bring about radial centering of the two body elements with reference to the second axis A2. Centering projection ZV and inner centering structure IZ can be rotated about the second axis A2 relative to one another. Centering can be advantageously combined with the narrowed progression of the outer surface of the side wall, by means of the lesser diameter of centering extension ZV and inner centering structure IZ, as compared with the diameter of the second threaded connection having the inside thread IG, and a lower but sufficient wall thickness around the cavity HR5 can be achieved.

The characteristics indicated above and in the claims, as well as evident from the figures, can advantageously be implemented not only individually but also in various combinations. The invention is not restricted to the exemplary embodiments described, but rather can be modified in many different ways, within the scope of the ability of a person skilled in the art.

The invention claimed is:

1. Abutment for a dental-prosthetic arrangement, the abutment:
having a fastening screw that can rotate about a first axis, on a first end on the implant side,
having a holding structure that determines a second axis, as a joining direction of a holding apparatus, on a second end on the prosthesis side, wherein the first axis and the second axis run at an incline relative to one another, as well as
having a tool opening disposed facing away from the first end, as an extension of the first axis, as access to the fastening screw,
wherein a first body element and a second body element are present,
wherein
the implant-side first end and the tool opening are formed on the first body element, and the holding structure is formed on the second body element,
the first body element and the second body element can be connected with one another by way of connection structures, and
the second body element covers the tool opening of the first body element, at least in part, in the connected state,
wherein the fastening screw has a fastening screw thread for forming a first threaded connection with the implant,
wherein the connection structures between the first body element and the second body element contain a screw connection having a second threaded connection around the second axis as the screw axis,
wherein the second threaded connection contains an inside thread on the inner surface of a side wall of the second body element,
wherein the first body element comprises a contact surface,
wherein as part of the second threaded connection the first body element further contains a threaded extension having an outside thread, the threaded extension projecting in a direction towards the second body element and projecting beyond the contact surface of the first body element,
wherein the side wall of the second body element comprises an end edge comprising a counter-surface,
wherein in the connected state of the first body element and the second body element, the counter-surface of the second body element is supported on the contact surface of the first body element,
wherein the first body element comprises a centering extension in a form of a non-annular circular cylinder having a face surface facing a direction along the second axis, the tool opening being formed in the face surface and protruding concavely into the face surface radially inwards towards the second axis, a stepped surface being formed between the threaded extension and the centering extension, and
wherein the centering extension is axially offset relative to the second threaded connection in a direction away from the threaded extension of the first body element such that the threaded extension of the first body element is disposed axially between the centering extension and the implant-side first end of the first body element.

2. Abutment according to claim 1, wherein in the connected state, the second body element completely covers the tool opening.

3. Abutment according to claim 1, wherein the second body element has a cavity that faces the first body element and is laterally delimited by the side wall that runs around the second axis.

4. Abutment according to claim 3, wherein the cavity is closed off on all sides, with the exception of an opening that faces the first body element.

5. Abutment according to claim 3, wherein the counter-surface of the second body element is ring-shaped.

6. Abutment according to claim 1, wherein the second threaded connection contains a fine thread having a thread pitch of maximally 0.5 mm.

7. Abutment according to claim 1, wherein the diameter of the second threaded connection is at least 20% larger than the diameter of the first threaded connection of the fastening screw.

8. Abutment according to claim 1, wherein the diameter of the second threaded connection amounts to at least 2 mm.

9. Abutment according to claim 1, wherein the holding structure forms a structure that can snap behind a counter-structure of a dental prosthesis.

10. Abutment according to claim 9, wherein the holding structure forms a radially projecting ring bead that runs around the second axis.

11. Abutment according to claim 9, wherein the holding structure forms a spherical head.

12. Abutment according to claim 1, wherein an anti-turn device is configured on the first, implant-side end of the first body element.

13. Abutment according to claim 1, wherein the second axis is inclined by at least 10° relative to the first axis.

14. Dental-prosthetic arrangement having a dental prosthesis and having at least one implant as well as an abutment according to claim 1 fastened onto the implant,
wherein the first body element of the abutment is fastened onto the implant via the fastening screw that engages into an inside thread of the implant, and
wherein the dental prosthesis is held on the abutment by way of the holding structure of the second body element.

15. Dental-prosthetic arrangement according to claim 14, wherein the dental prosthesis can be released from the holding structure of the abutment or set onto it, without tools, in the direction of the second axis.

16. Dental-prosthetic arrangement according to claim 15, wherein when the dental prosthesis is released from the abutment, the second body element, with the holding structure, can be released from the first body element, without destruction and without any change in position of the first body element.

* * * * *